(12) United States Patent
Rowney et al.

(10) Patent No.: US 11,484,486 B2
(45) Date of Patent: Nov. 1, 2022

(54) COSMETIC CLEANSING COMPOSITIONS

(71) Applicant: THE BOOTS COMPANY PLC, Nottingham (GB)

(72) Inventors: Jamie Rowney, Nottingham (GB); Christopher John Elms, Nottingham (GB)

(73) Assignee: THE BOOTS COMPANY PLC, Nottingham (GB)

( * ) Notice: Subject to any disclaimer, the term of this patent is extended or adjusted under 35 U.S.C. 154(b) by 196 days.

(21) Appl. No.: 16/490,204

(22) PCT Filed: Feb. 28, 2018

(86) PCT No.: PCT/EP2018/025049
§ 371 (c)(1),
(2) Date: Aug. 30, 2019

(87) PCT Pub. No.: WO2018/157974
PCT Pub. Date: Sep. 7, 2018

(65) Prior Publication Data
US 2021/0196604 A1    Jul. 1, 2021

(30) Foreign Application Priority Data
Mar. 1, 2017 (EP) ................................. 17020081.0

(51) Int. Cl.
*A61K 8/00* (2006.01)
*A61K 8/46* (2006.01)
(Continued)

(52) U.S. Cl.
CPC ............... *A61K 8/466* (2013.01); *A61K 8/42* (2013.01); *A61K 8/44* (2013.01); *A61K 8/60* (2013.01);
(Continued)

(58) Field of Classification Search
CPC . A61K 8/466; A61K 8/42; A61K 8/44; A61K 2800/30
See application file for complete search history.

(56) References Cited

U.S. PATENT DOCUMENTS 6,723,688 B1 *   4/2004   Malik .................... A61K 8/442
                                                      510/130
9,018,150 B1     4/2015   Rizk
(Continued)

FOREIGN PATENT DOCUMENTS

DE    102 59 401 A1    7/2004
EP      2932960 A1    10/2015
JP     H0348608 A     3/1991

OTHER PUBLICATIONS

International Preliminary Report on Patentability, corresponding International Application No. PCT/EP2018/025049, dated Feb. 22, 2019.

(Continued)

*Primary Examiner* — Necholus Ogden, Jr.
(74) *Attorney, Agent, or Firm* — Marshall, Gerstein & Borun LLP

(57) ABSTRACT

According to the present invention there is provided a cosmetic composition comprising a cosmetically acceptable carrier and a surfactant system consisting of: (i) an anionic surfactant; (ii) an amphoteric surfactant; and (iii) a non-ionic surfactant, wherein the anionic surfactant is present in an amount of from about 0.5% to about 25% by weight of the surfactant system, wherein the amphoteric surfactant is present in an amount of from about 0.5% to about 50% by weight of the surfactant system, wherein the non-ionic surfactant is present in an amount of from about 0.5% to about 45% (e.g. 43%) by weight of the surfactant system, and wherein the total amount of the surfactant system present in the cosmetic composition is from about 1.5% to about 25% by weight of the composition.

6 Claims, 2 Drawing Sheets

Figure 2:
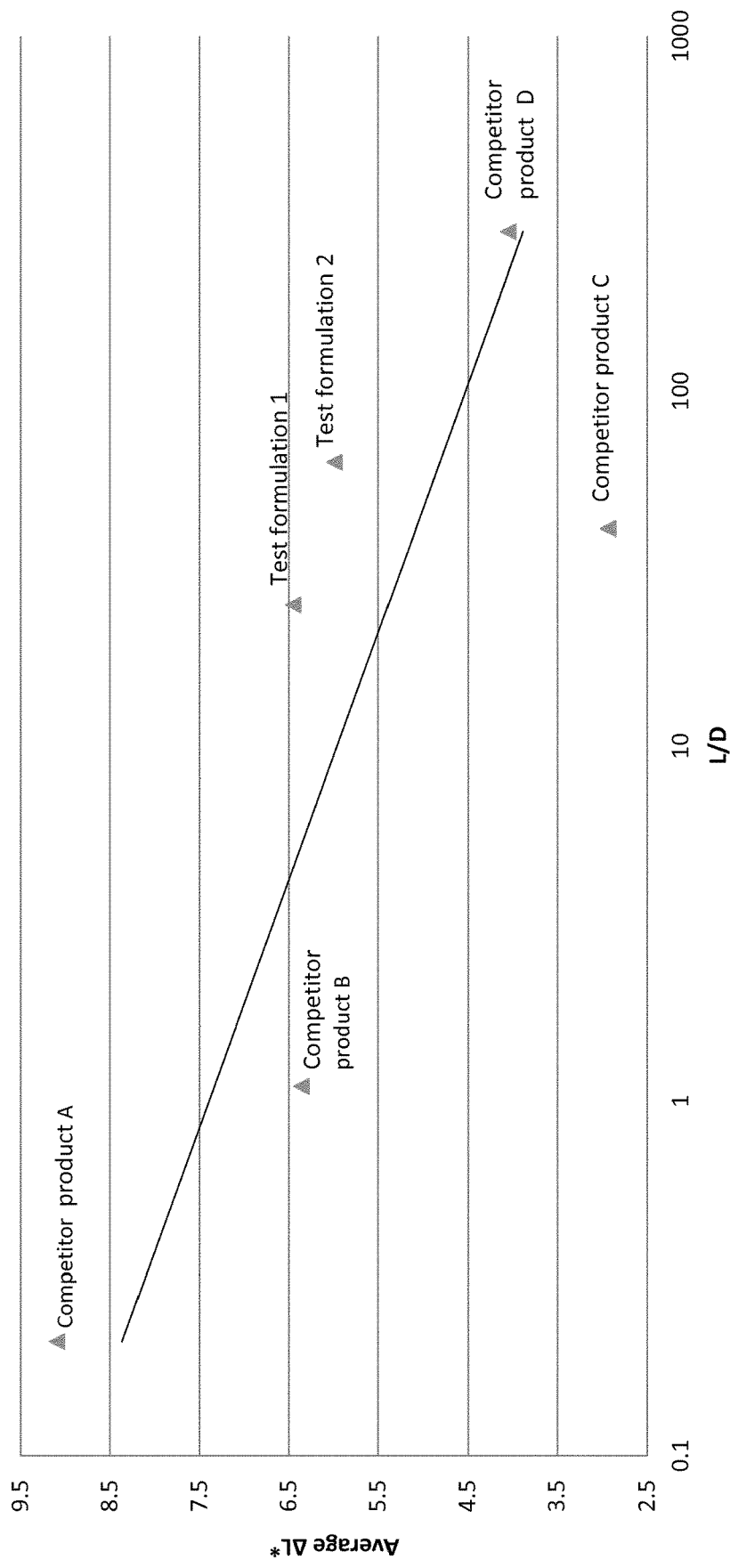

(51) Int. Cl.
   *A61K 8/42*  (2006.01)
   *A61K 8/44*  (2006.01)
   *A61K 8/60*  (2006.01)
   *A61Q 1/14*  (2006.01)
   *A61Q 19/10* (2006.01)

(52) U.S. Cl.
   CPC ............... *A61K 8/602* (2013.01); *A61Q 1/14* (2013.01); *A61Q 19/10* (2013.01); *A61K 2800/30* (2013.01)

(56) References Cited

U.S. PATENT DOCUMENTS

| | | |
|---|---|---|
| 2014/0039066 A1 | 2/2014 | Grimadell et al. |
| 2014/0349902 A1* | 11/2014 | Allef ................ A61K 8/361 510/119 |
| 2016/0095804 A1 | 4/2016 | Xavier et al. |

OTHER PUBLICATIONS

International Search Report and Written Opinion, corresponding International Application No. PCT/EP2018/025049, dated May 4, 2018.

European Communication Rule 114-2 Observation for EP Application No. 18709925.4-112, dated Apr. 19, 2021, 7 pages.

\* cited by examiner

Figure 1

|  | Example formulations | | | |
| Material name | A | B | C | D |
| --- | --- | --- | --- | --- |
| Aqua | Q.S. | Q.S. | Q.S. | Q.S. |
| Glycerin | 4.2000 | 7.2900 | 6.2000 | 6.0900 |
| Butylene Glycol | 0.3000 | 0.3000 | 0.4000 | |
| Disodium Lauryl Sulfosuccinate | | | 0.8800 | 0.8800 |
| Disodium laureth sulfosuccinate | | 3.0000 | | |
| Sodium Cocoyl Glutamate | 4.0800 | | | |
| Laureth-7 Citrate | | | 2.1200 | 1.8905 |
| Cocamidopropyl betaine | | 1.9800 | 4.2000 | 7.0000 |
| Sodium cocoamphoacetate | 6.8700 | 2.2000 | 2.8000 | |
| Decyl Glucoside | | 4.5000 | | |
| Lauryl glucoside | 5.9000 | | | |
| Coco-glucoside | 0.8750 | 0.8750 | 5.2300 | 5.2300 |
| Glyceryl laurate | | | | 0.2000 |
| Glyceryl oleate | 0.7500 | 0.7500 | 0.9000 | 0.9000 |
| PEG-40 hydrogenated castor oil | | | | 0.5000 |
| PEG-200 hydrogenated glyceryl palmate | | | | 0.5000 |
| PEG-7 glyceryl cocoate | | | | 0.2000 |
| PEG-18 Glyceryl Oleate/Cocoate | 4.2500 | | | |
| Hydrogenated palm glycerides citrate | 0.0002 | 0.0018 | 0.0002 | 0.0002 |
| Polyacrylate Crosspolymer-6 | | 1.2350 | | |
| Acrylates Copolymer | | | 2.7000 | |
| Xanthan gum | | 0.3000 | | |
| Citric acid | 0.5150 | 0.5150 | 0.0505 | 0.0505 |
| Potassium hydroxide | 0.0110 | 0.0110 | 0.1150 | 0.1150 |
| Sodium Hydroxide | | | 0.7000 | |
| Tetrasodium EDTA | 0.0860 | 0.0860 | 0.0860 | 0.0860 |
| Phenoxyethanol | 0.5000 | 0.5000 | 0.5000 | 0.5000 |
| Sodium benzoate | 0.1500 | 0.1763 | 0.1500 | 0.1500 |
| Panthenol | | | | 0.1875 |
| Ascorbyl glucoside | | 0.1000 | 0.1000 | 0.1000 |
| Ascorbyl palmitate | | 0.0074 | 0.0007 | 0.0007 |
| Betaine | 0.5000 | | | 0.5000 |
| Bisabolol | | | 0.0500 | 0.0500 |
| Arctium Lappa extract | | | 0.1400 | |
| Camellia sinensis leaf extract | | | | 0.0010 |
| Panax Ginseng Extract | 0.2000 | 0.2000 | | |
| Lecithin | 0.0006 | 0.0006 | 0.0007 | 0.0007 |
| Tocopherol | 0.0004 | 0.0004 | 0.0004 | 0.0004 |

COSMETIC CLEANSING COMPOSITIONS

FIELD OF THE INVENTION

The present invention relates to cosmetic cleansing compositions and methods of cosmetic cleansing treatment using said compositions.

BACKGROUND TO THE INVENTION

It is common practice to use cosmetic compositions based on surfactants for cleansing the skin and/or hair. These compositions typically contain substantial amounts of surfactants in order to be able to provide compositions with good washing power. Good washing power is important to effectively cleanse the skin from a variety of both exogenous and endogenous insults. Exogenous insults include those arising from the environment such as ultraviolet radiation (UVA and UVB), infra-red and visible light, atmospheric pollution (including cigarette smoke) and/or harsh chemicals including surfactants in cosmetic formulations. Such environmental factors may either directly or indirectly result in skin damage by the generation of reactive species and free radicals, for example superoxide anions, hydrogen peroxide, hydroxyl ions, peroxyl ions, ozone, singlet oxygen, sulphur oxide, nitrogen oxide, carbon monoxide, alkoxyl ion, peroxynitrite and heavy metals. Reactive oxygen species (ROS), reactive carbonyl species (RCS) and reactive nitrogen species (RNS) need to be particularly considered. Endogenous insults can also result in skin damage, for example hormonal fluctuations (e.g. cortisol and adrenaline hormones), aging and other biochemical changes from within the skin.

With respect to atmospheric pollution (including cigarette smoke), polycyclic aromatic hydrocarbons (PAHs) are key pollutants that cause skin damage through a number of different mechanisms including increased melanocyte activation, increased sebum oxidation and mitochondrial damage of keratinocytes and fibroblasts. PAHs can also increase ROS discussed above in the skin.

However, although these compositions have good washing power, they have poor skin and hair compatibility and are aggressive. Use over time causes skin and hair damage or dryness which is particularly associated with the removal of proteins and lipids contained in or on the skin or hair surface.

Individuals may find that current skin cleansers cause skin imbalance, e.g. cleansers with strong washing power cause skin dryness and tightness, whilst cleansers with weak washing power result in blocked pores. If an individual consistently uses the same cleanser over a period of time skin health and appearance would fluctuate. Therefore the individual can get caught in a cycle of needing to use varying cleansers to each, in turn, compensate for the effects of the previous cleanser.

SUMMARY OF THE INVENTION

Thus, there is a consumer need to provide cosmetic cleansing compositions, which have good washing power and which are tolerated well by the skin and/or hair.

The Applicants have identified cosmetic compositions which effectively cleanse the skin and/or hair while maintaining mildness. The Applicants have surprisingly found that the presence of a specific surfactant system makes it possible to achieve an optimal balance between cleansing efficacy and mildness. This enables an individual to use said compositions consistently on a regular basis whilst still maintaining good skin health and appearance.

Accordingly, in a first aspect of the invention there is provided a cosmetic composition comprising a cosmetically acceptable carrier and a surfactant system consisting of:
  (i) an anionic surfactant;
  (ii) an amphoteric surfactant; and
  (iii) a non-ionic surfactant,
wherein the anionic surfactant is present in an amount of from about 0.5% to about 25% (e.g. 22%) by weight of the surfactant system,
wherein the amphoteric surfactant is present in an amount of from about 0.5% to about 50% by weight of the surfactant system,
wherein the non-ionic surfactant is present in an amount of from about 0.5% to about 45% (e.g. 43%) by weight of the surfactant system, and
wherein the total amount of the surfactant system present in the cosmetic composition is from about 1.5% to about 25% by weight of the composition.

Surprisingly it has been found that use of a specific combination of an anionic, an amphoteric and a non-ionic surfactant at defined levels, provides an improved cleansing experience for the user in that adequate cleansing can be achieved whilst preventing or reducing harshness, damage or irritation to the skin and/or hair. Despite the overall surfactant level being low, adequate cleansing can still be achieved.

In another aspect of the invention, there is provided a method of cosmetic cleansing treatment of the skin and/or hair comprising the step of applying the cosmetic composition according to the invention to the skin and/or hair.

In another aspect of the invention, there is provided use of the cosmetic composition according to the invention as a topical application for cleansing the skin and/or hair, and/or for removing makeup.

It is appreciated that the cosmetic compositions of the present invention can be effective in removing pollutants from the skin and thus cosmetically prevent the detrimental effects of pollution insult to the skin. Alternatively, the cosmetic compositions of the present invention can prevent further pollutants from penetrating skin that had been previously damaged as a result of pollution insult, allowing the skin to repair itself and in effect leading to the cosmetic compositions of the present invention cosmetically treating skin damage as a result of pollution insult. Thus, a further aspect of the present invention provides a method of cosmetically treating skin damage as a result of pollution insult or of cosmetically preventing the detrimental effects of pollution to the skin, said method comprising cleansing the skin with an effective amount of cosmetic composition.

DETAILED DESCRIPTION OF THE INVENTION

The term "surfactant" as used herein is intended to mean a molecule having both hydrophilic (polar) and hydrophobic (non-polar) groups, as would be understood by a person skilled in the art.

The invention makes use of an anionic surfactant. The term "anionic surfactant" is intended to mean a surfactant comprising an anionic hydrophilic group, i.e. a group bearing at least one permanent negative charge or a group capable of being ionised as a negatively charged species under the conditions of use of the cosmetic composition of the invention (for example by the medium or the pH).

The anionic surfactant may be a sulfosuccinate, a carboxylate, a glutamate, a citrate, an isethionate, a glycinate, a sulfolaurate, a taurate, or a combination thereof. In one embodiment, the anionic surfactant is not a sulphate or a sulfonate. The anionic surfactants may be in the form of a salt, for example a sodium salt, a disodium salt and/or a magnesium salt. The anionic surfactant may have a hydrophobic chain of C8-C30, C10-C28, C12-C26, C10-C18, C12-C24, or C12-18.

The anionic surfactant may be selected from the group consisting of Disodium Laureth Sulfosuccinate, Disodium Lauryl Sulfosuccinate, Laureth-7 Citrate, Sodium Cocoyl Glutamate, Sodium Lauroyl Sarcosinate, Sodium Lauryl Glucose Carboxylate, Disodium Cocamido MIPA Sulfosuccinate, Disodium Cocoyl Glutamate, Disodium Oleamido MEA Sulfosuccinate, Disodium PEG-4 Cocamido MIPA-Sulfosuccinate, Disodium PEG-5 Laurylcitrate Sulfosuccinate, Disodium Ricinoleamido MEA-Sulfosuccinate, Disodium Undecylenamido MEA-Sulfosuccinate, Sodium C12-13 Pareth-8 Carboxylate, Sodium C12-15 Pareth-12 Carboxylate, Sodium Laureth-11 Carboxylate, Sodium Laureth-5 Carboxylate, Sodium Lauroyl Glutamate, Sodium Stearoyl Glutamate, Sodium Cocoyl Isethionate, Sodium Isethionate, Sodium Lauroyl Glycinate, Sodium Lauroyl Methyl Isethionate, Sodium Lauryl Glycinate, Sodium Methyl 2-Sulfolaurate, Sodium Methyl Cocoyl Taurate, Sodium Methyl, Lauroyl Taurate, Sodium Methyl Oleoyl Taurate, TEA-Cocoyl Glutamate, and combinations thereof.

The anionic surfactant may be selected from the group consisting of Disodium Laureth Sulfosuccinate, Disodium Lauryl Sulfosuccinate, Laureth-7 Citrate, Sodium Cocoyl Glutamate, Sodium Lauroyl Sarcosinate, Sodium Lauryl Glucose Carboxylate, Disodium Cocamido MIPA Sulfosuccinate, Disodium Cocoyl Glutamate, Disodium Oleamido MEA Sulfosuccinate, Disodium PEG-4 Cocamido MIPA-Sulfosuccinate, Disodium PEG-5 Laurylcitrate Sulfosuccinate, Disodium Ricinoleamido MEA-Sulfosuccinate, Disodium Undecylenamido MEA-Sulfosuccinate, Sodium C12-13 Pareth-8 Carboxylate, Sodium C12-15 Pareth-12 Carboxylate, Sodium Laureth-11 Carboxylate, Sodium Laureth-5 Carboxylate, Sodium Lauroyl Glutamate, Sodium Stearoyl Glutamate, and combinations thereof.

The anionic surfactant may be selected from the group consisting of Disodium Laureth Sulfosuccinate, Disodium Lauryl Sulfosuccinate, Laureth-7 Citrate, Sodium Cocoyl Glutamate, Sodium Lauroyl Sarcosinate, Sodium Lauryl Glucose Carboxylate, and combinations thereof.

The anionic surfactant may be present in an amount of from about 5% to about 25% (e.g. 22%) by weight relative to the total weight of the surfactant system, for example from about 7% to about 25% (e.g. 22%), or from about 10% to about 25% (e.g. 22%), or from about 12% to about 25% (e.g. 22%), or from about 15% to about 25% (e.g. 22%), or from about 17% to about 25% (e.g. 22%), or from about 20% to about 25% (e.g. 22%), or from about 17% to about 24%, or from about 18% to about 23% (e.g. 22%), or from about 19% to about 22% by weight relative to the total weight of the surfactant system.

The anionic surfactant may be present in an amount of from about 0.5% to about 25% (e.g. 22%) by weight relative to the total weight of the surfactant system, for example from about 0.5% to about 24%, or from about 0.5% to about 23%, or from about 1% to about 22%, or from about 1% to about 21%, or from about 2% to about 20%, or from about 2% to about 19%, or from about 3% to about 18%, or from about 3% to about 17%, or from about 3% to about 16%, or from about 5% to about 15% by weight relative to the total weight of the surfactant system.

The anionic surfactant may be present in an amount of from about 0.01% to about 6% by weight relative to the total weight of the composition, for example from about 0.5% to about 6%, or from about 0.5% to about 5%, or from about 0.5% to about 4%, or from about 1% to about 6%, or from about 2% to about 6%, or from about 3% to about 6%, or from about 2% to about 5%, or from about 3% to about 5% by weight relative to the total weight of the composition.

The invention makes use of an amphoteric surfactant. The term "amphoteric surfactant" (also known as a "zwitterionic surfactant") is intended to mean a surfactant comprising a hydrophilic group with both cationic and anionic groups.

The amphoteric surfactant may be a betaine, a hydroxysultaine, a diacetate, an acetate, or a combination thereof. The amphoteric surfactants may be in the form of a salt, for example a sodium salt, a disodium salt and/or a magnesium salt. The amphoteric surfactant may have a hydrophobic chain of C8-C30, C10-C28, C12-C26, C10-C18, C12-C24, or C12-18.

The amphoteric surfactant may be selected from the group consisting of Capryl/Capramidopropyl Betaine, Cocamidopropyl Betaine, Sodium Cocoamphoacetate, Babassuamidopropyl Betaine, Cetyl Betaine, Coco-Betaine, Disodium Capryloamphodiacetate, Disodium Cocoamphodiacetate, Disodium Lauroamphodiacetate, Lauramidopropyl Betaine, Lauryl Betaine, Meadowfoamamidopropyl Betaine, Oleamidopropyl Betaine, SheaButteramidopropyl Betaine, Sodium Cocoabutteramphoacetate, Sodium Lauroamphoacetate, Sodium Olivamphoacetate, Soyamidopropyl Betaine, Cocamidopropyl Hydroxysultaine, Lauramidopropyl Hydroxysultaine, Lauryl Hydroxysultaine, and combinations thereof.

The amphoteric surfactant may be selected from the group consisting of Capryl/Capramidopropyl Betaine, Cocamidopropyl Betaine, Sodium Cocoamphoacetate, Babassuamidopropyl Betaine, Cetyl Betaine, Coco-Betaine, Disodium Capryloamphodiacetate, Disodium Cocoamphodiacetate, Disodium Lauroamphodiacetate, Lauramidopropyl Betaine, Lauryl Betaine, Meadowfoamamidopropyl Betaine, Oleamidopropyl Betaine, SheaButteramidopropyl Betaine, Sodium Cocoabutteramphoacetate, Sodium Lauroamphoacetate, Sodium Olivamphoacetate, Soyamidopropyl Betaine, and combinations thereof.

The amphoteric surfactant may be selected from the group consisting of Capryl/Capramidopropyl Betaine, Cocamidopropyl Betaine, Sodium Cocoamphoacetate, and combinations thereof.

The amphoteric surfactant may be present in an amount of from about 5% to about 50% by weight relative to the total weight of the surfactant system, for example from about 10% to about 50%, or from about 15% to about 50%, or from about 20% to about 50%, or from about 30% to about 50%, or from about 35% to about 50%, or from about 40% to about 50%, or from about 42% to about 50%, or from about 44% to about 50%, or from about 45% to about 50%, or from about 37% to about 48%, or from about 40% to about 47%, or from about 40% to about 46%, or from about 42% to about 46% by weight relative to the total weight of the surfactant system.

The amphoteric surfactant may be present in an amount of from about 0.5% to about 50% by weight relative to the total weight of the surfactant system, for example from about 1% to about 50%, or from about 1% to about 49%, or from about 1% to about 48%, or from about 2% to about 48%, or from about 2% to about 47%, or from about 3% to about 46% by weight relative to the total weight of the surfactant system.

The amphoteric surfactant may be present in an amount of from about 0.01% to about 12% by weight relative to the total weight of the composition, for example from about 0.5% to about 10%, or from about 0.5% to about 8%, or from about 0.5% to about 7%, or from about 1% to about 8%, or from about 2% to about 8%, or from about 3% to about 8%, or from about 3% to about 7%, or from about 4% to about 7% by weight relative to the total weight of the composition.

The invention makes use of a non-ionic surfactant. The term "non-ionic surfactant" is intended to mean a surfactant comprising a non-ionic hydrophilic group, i.e. a group having no electric charge.

The non-ionic surfactant may be a glucoside. The non-ionic surfactant may have a hydrophobic chain of C8-C30, C10-C28, C12-C26, C10-C18, C12-C24, or C12-18.

The non-ionic surfactant may be selected from the group consisting of Coco Glucoside, Lauryl Glucoside, Caprylyl/Capryl Glucoside, Decyl Glucoside, Polyglyceryl-4 Cocoate, and combinations thereof.

The non-ionic surfactant may be selected from the group consisting of Coco Glucoside, Lauryl Glucoside, Caprylyl/Capryl Glucoside, Decyl Glucoside, and combinations thereof.

The non-ionic surfactant may be selected from the group consisting of Coco Glucoside, Lauryl Glucoside, and combinations thereof.

The non-ionic surfactant may be present in an amount of from about 5% to about 45% (e.g. 43%) by weight relative to the total weight of the surfactant system, for example from about 10% to about 45% (e.g. 43%), or from about 15% to about 45% (e.g. 43%), or from about 20% to about 45% (e.g. 43%), or from about 30% to about 45% (e.g. 43%), or from about 30% to about 40%, or from about 30% to about 36%, or from about 30% to about 35%, or from about 25% to about 35%, or from about 28% to about 37%, or from about 28% to about 35%, or from about 29% to about 34% by weight relative to the total weight of the surfactant system.

The non-ionic surfactant may be present in an amount of from about 0.5% to about 45% (e.g. 43%) by weight relative to the total weight of the surfactant system, for example from about 1% to about 45%, or from about 1% to about 44%, or from about 1% to about 43%, or from about 2% to about 42%, or from about 2% to about 40%, or from about 3% to about 40%, or from about 3% to about 37%, or from about 3% to about 35% by weight relative to the total weight of the surfactant system.

The non-ionic surfactant may be present in an amount of from about 0.01% to about 8% by weight relative to the total weight of the composition, for example from about 0.5% to about 7%, or from about 0.5% to about 6%, or from about 1% to about 6%, or from about 2% to about 6%, or from about 3% to about 6%, or from about 4% to about 6%, or from about 4% to about 8%, or from about 4% to about 7% by weight relative to the total weight of the composition.

The amphoteric surfactant may be present in an amount of at least the same amount as the anionic surfactant. In one embodiment the amphoteric surfactant is present in an amount of about 4 times or less the amount of the anionic surfactant, for example about 3.9 times or less, about 3.8 times or less, about 3.7 times or less, about 3.6 times or less, about 3.5 times or less, about 3.4 times or less, about 3.3 times or less, about 3.2 times or less, about 3.1 times or less, about 3 times or less, about 2.9 times or less, about 2.8 times or less, about 2.7 times or less, about 2.6 times or less, about 2.5 times or less, about 2.4 times or less, or about 2.3 times or less.

The non-ionic surfactant may be present in an amount of at least the same amount as the anionic surfactant. In one embodiment the non-ionic surfactant is present in an amount of about 4 times or less the amount of the anionic surfactant, for example about 3.9 times or less, about 3.8 times or less, about 3.7 times or less, about 3.6 times or less, about 3.5 times or less, about 3.4 times or less, about 3.3 times or less, about 3.2 times or less, about 3.1 times or less, about 3 times or less, about 2.9 times or less, about 2.8 times or less, about 2.7 times or less, about 2.6 times or less, about 2.5 times or less, about 2.4 times or less, about 2.3 times or less, about 2.2 times or less, about 2.1 times or less, about 2 times or less, about 1.9 times or less, about 1.8 times or less, or about 1.7 times or less.

The amphoteric surfactant may be present in an amount of at least the same amount as the non-ionic surfactant. In one embodiment the amphoteric surfactant is present in an amount of about 4 times or less the amount of the non-ionic surfactant, for example about 3.9 times or less, about 3.8 times or less, about 3.7 times or less, about 3.6 times or less, about 3.5 times or less, about 3.4 times or less, about 3.3 times or less, about 3.2 times or less, about 3.1 times or less, about 3 times or less, about 2.9 times or less, about 2.8 times or less, about 2.7 times or less, about 2.6 times or less, about 2.5 times or less, about 2.4 times or less, about 2.3 times or less, about 2.2 times or less, about 2.1 times or less, about 2 times or less, about 1.9 times or less, about 1.8 times or less, about 1.7 times or less, about 1.6 times or less, about 1.5 times or less, or about 1.4 times or less.

In one embodiment, the amphoteric surfactant may be present in an amount more than the amount of the anionic surfactant. In one embodiment, the amphoteric surfactant may be present in an amount more than the amount of the non-ionic surfactant. In one embodiment, the non-ionic surfactant may be present in an amount more than the amount of the anionic surfactant.

The anionic surfactant, amphoteric surfactant and non-ionic surfactant making up the surfactant system add up to 100%. The cosmetic composition of the invention may comprise the surfactant system in an amount of from about 5% to about 25% by weight of the composition, for example from about 5% to about 22%, from about 5% to about 20%, from about 5% to about 15%, from about 7% to about 22%, from about 10% to about 22%, from about 10% to about 20%, from about 12% to about 18%, or from about 10% to about 15% by weight of the composition.

The cosmetic composition of the invention may comprise the surfactant system in an amount of from about 2% to about 25% by weight of the composition, for example from about 2% to about 24%, from about 2% to about 20%, from about 3% to about 18%, from about 3% to about 17%, from about 4% to about 16% by weight of the composition.

In one embodiment, the amphoteric surfactant is present in an amount 3 times or less the amount of the anionic surfactant and the non-ionic surfactant is present in an amount 2.5 times or less the amount of the anionic surfactant and the amphoteric surfactant is present in an amount 2 times or less the amount of the non-ionic surfactant. In one embodiment, the amphoteric surfactant is present in an amount 2.5 times or less the amount of the anionic surfactant and the non-ionic surfactant is present in an amount 2 times or less the amount of the anionic surfactant and the amphoteric surfactant is present in an amount 1.5 times or less the amount of the non-ionic surfactant. In one embodiment, the amphoteric surfactant is present in an amount 2.4 times or less the amount of the anionic surfactant and the non-ionic surfactant is present in an amount 1.9 times or less the amount of the anionic surfactant and the amphoteric surfactant is present in an amount 1.4 times or less the amount of the non-ionic surfactant. In one embodiment, the amphoteric surfactant is present in an amount 2.3 times or less the amount of the anionic surfactant and the non-ionic surfactant is present in an amount 1.8 times or less the amount of the anionic surfactant and the amphoteric surfactant is present in an amount 1.4 times or less the amount of the non-ionic surfactant.

In one embodiment, the cosmetic composition of the invention does not further comprise any additional surfactants. In one embodiment, the only surfactants present in the cosmetic composition of the invention are those present in the surfactant system. In one embodiment, the cosmetic composition does not comprise a cationic surfactant. In one embodiment the cosmetic composition of the invention may further comprise one or more surfactants. These may be different to the surfactants present in surfactant system. In one embodiment where one or more such surfactants are present in the cosmetic composition, the one or more surfactants are present in an amount of from about 0.01% to about 5% by weight of the composition.

In one embodiment, the cosmetic composition of the invention comprises a cosmetically acceptable carrier and a surfactant system consisting of:
 (i) an anionic surfactant;
 (ii) an amphoteric surfactant; and
 (iii) a non-ionic surfactant,
wherein the anionic surfactant is present in an amount of from about 0.5% to about 25% (e.g. about 5% to about 25%, about 10% to about 22%, about 0.5% to about 22% or about 5% to about 22%) by weight of the surfactant system,
wherein the amphoteric surfactant is present in an amount of from about 0.5% to about 50% (e.g. about 5% to about 50%, about 35% to about 50%) by weight of the surfactant system,
wherein the non-ionic surfactant is present in an amount of from about 0.5% to about 45% (e.g. about 5% to about 45%, about 25% to about 35%, about 0.5% to about 43%, about 5% to about 43%) by weight of the surfactant system, and
wherein the total amount of the surfactant system present in the cosmetic composition is from about 1.5% to about 25% (e.g. about 5% to about 25%, about 10% to about 15%) by weight of the composition.

In one embodiment, the cosmetic composition of the invention comprises a cosmetically acceptable carrier and a surfactant system consisting of:
 (i) an anionic surfactant;
 (ii) an amphoteric surfactant; and
 (iii) a non-ionic surfactant,
wherein the anionic surfactant is present in an amount of from about 0.5% to about 25% (e.g. about 5% to about 25%, about 10% to about 22%, about 0.5% to about 22% or about 5% to about 22%) by weight of the surfactant system,
wherein the amphoteric surfactant is present in an amount of from about 0.5% to about 50% (e.g. about 5% to about 50%, about 35% to about 50%) by weight of the surfactant system,
wherein the non-ionic surfactant is present in an amount of from about 0.5% to about 45% (e.g. about 5% to about 45%, about 25% to about 35%, about 0.5% to about 43% or about 5% to about 43%) by weight of the surfactant system,
wherein the amphoteric surfactant is present in an amount 3 times or less (e.g. about 2.5 times or less or 2.3 times or less) the amount of the anionic surfactant and the non-ionic surfactant is present in an amount 2.5 times or less (e.g. 2 times or less, or 1.7 times or less) the amount of the anionic surfactant and the amphoteric surfactant is present in an amount 2 times or less (e.g. 1.7 times or less or 1.5 times or less) the amount of the non-ionic surfactant, and
wherein the total amount of the surfactant system present in the cosmetic composition is from about 1.5% to about 25% (e.g. about 5% to about 25%, about 10% to about 15%) by weight of the composition.

In one embodiment, the cosmetic composition of the invention comprises a cosmetically acceptable carrier and a surfactant system consisting of:
 (i) an anionic surfactant;
 (ii) an amphoteric surfactant; and
 (iii) a non-ionic surfactant selected from the group consisting of Coco Glucoside, Lauryl Glucoside, Caprylyl/Capryl Glucoside, Decyl Glucoside, Polyglyceryl-4 Cocoate, and combinations thereof,
wherein the anionic surfactant is present in an amount of from about 0.5% to about 25% (e.g. about 5% to about 25%, about 10% to about 22%, about 0.5% to about 22% or about 5% to about 22%) by weight of the surfactant system,
wherein the amphoteric surfactant is present in an amount of from about 0.5% to about 50% (e.g. about 5% to about 50%, about 35% to about 50%) by weight of the surfactant system,
wherein the non-ionic surfactant is present in an amount of from about 0.5% to about 45% (e.g. about 5% to about 45%, about 25% to about 35%, about 0.5% to about 43% or about 5% to about 43%) by weight of the surfactant system, and
wherein the total amount of the surfactant system present in the cosmetic composition is from about 1.5% to about 25% (e.g. about 5% to about 25%, about 10% to about 15%) by weight of the composition.

In one embodiment, the cosmetic composition of the invention comprises a cosmetically acceptable carrier and a surfactant system consisting of:
 (i) an anionic surfactant selected from the group consisting of Disodium Laureth Sulfosuccinate, Disodium Lauryl Sulfosuccinate, Laureth-7 Citrate, Sodium Cocoyl Glutamate, Sodium Lauroyl Sarcosinate, Sodium Lauryl Glucose Carboxylate, Disodium Cocamido MIPA Sulfosuccinate, Disodium Cocoyl Glutamate, Disodium Oleamido MEA Sulfosuccinate, Disodium PEG-4 Cocamido MIPA-Sulfosuccinate, Disodium PEG-5 Laurylcitrate Sulfosuccinate, Disodium Ricinoleamido MEA-Sulfosuccinate, Disodium Undecylenamido MEA-Sulfosuccinate, Sodium C12-13 Pareth-8 Carboxylate, Sodium C12-15 Pareth-12 Carboxylate, Sodium Laureth-11 Carboxylate, Sodium Laureth-5 Carboxylate, Sodium Lauroyl Glutamate, Sodium Stearoyl Glutamate, Sodium Cocoyl Isethionate, Sodium Isethionate, Sodium Lauroyl Glycinate, Sodium Lauroyl Methyl Isethionate, Sodium Lauryl Glycinate, Sodium Methyl 2-Sulfolaurate, Sodium Methyl Cocoyl Taurate, Sodium Methyl, Lauroyl Taurate, Sodium Methyl Oleoyl Taurate, TEA-Cocoyl Glutamate, and combinations thereof;
 (ii) an amphoteric surfactant selected from the group consisting of Capryl/Capramidopropyl Betaine, Cocamidopropyl Betaine, Sodium Cocoamphoacetate, Babassuamidopropyl Betaine, Cetyl Betaine, Coco-Betaine, Disodium Capryloamphodiacetate, Disodium Cocoamphodiacetate, Disodium Lauroamphodiacetate, Lauramidopropyl Betaine, Lauryl Betaine, Meadowfoamamidopropyl Betaine, Oleamidopropyl Betaine, SheaButteramidopropyl Betaine, Sodium Cocoabutteramphoacetate, Sodium Lauroamphoacetate, Sodium Olivamphoacetate, Soyamidopropyl Betaine, Cocamidopropyl Hydroxysultaine, Lauramidopropyl Hydroxysultaine, Lauryl Hydroxysultaine, and combinations thereof; and (iii) a non-ionic surfactant selected from the group consisting of Coco Glucoside, Lauryl Glucoside, Caprylyl/Capryl Glucoside, Decyl Glucoside, Polyglyceryl-4 Cocoate, and combinations thereof, wherein the anionic surfactant is present in an amount of from about 0.5% to about 25% (e.g. about 5% to about 25%, about 10% to about 22%, about 0.5% to about 22% or about 5% to about 22%) by weight of the surfactant system, wherein the amphoteric surfactant is present in an amount of from about 0.5% to about 50% (e.g. about 5% to about 50%, about 35% to about 50%) by weight of the surfactant system, wherein the non-ionic surfactant is present in an amount of from about 0.5% to about 45% (e.g. about 5% to about 45%, about 25% to about 35%, about 0.5% to about 43% or about 5% to about 43%) by weight of the surfactant system, and wherein the total amount of the surfactant system present in the cosmetic composition is from about 1.5% to about 25% (e.g. about 5% to about 25%, about 10% to about 15%) by weight of the composition.

In one embodiment, the cosmetic composition of the invention comprises a cosmetically acceptable carrier and a surfactant system consisting of:

(i) an anionic surfactant selected from the group consisting of Disodium Laureth Sulfosuccinate, Disodium Lauryl Sulfosuccinate, Laureth-7 Citrate, Sodium Cocoyl Glutamate, Sodium Lauroyl Sarcosinate, Sodium Lauryl Glucose Carboxylate, Disodium Cocamido MIPA Sulfosuccinate, Disodium Cocoyl Glutamate, Disodium Oleamido MEA Sulfosuccinate, Disodium PEG-4 Cocamido MIPA-Sulfosuccinate, Disodium PEG-5 Laurylcitrate Sulfosuccinate, Disodium Ricinoleamido MEA-Sulfosuccinate, Disodium Undecylenamido MEA-Sulfosuccinate, Sodium C12-13 Pareth-8 Carboxylate, Sodium C12-15 Pareth-12 Carboxylate, Sodium Laureth-11 Carboxylate, Sodium Laureth-5 Carboxylate, Sodium Lauroyl Glutamate, Sodium Stearoyl Glutamate, and combinations thereof;

(ii) an amphoteric surfactant selected from the group consisting of Capryl/Capramidopropyl Betaine, Cocamidopropyl Betaine, Sodium Cocoamphoacetate, Babassuamidopropyl Betaine, Cetyl Betaine, CocoBetaine, Disodium Capryloamphodiacetate, Disodium Cocoamphodiacetate, Disodium Lauroamphodiacetate, Lauramidopropyl Betaine, Lauryl Betaine, Meadowfoamamidopropyl Betaine, Oleamidopropyl Betaine, SheaButteramidopropyl Betaine, Sodium Cocoabutteramphoacetate, Sodium Lauroamphoacetate, Sodium Olivamphoacetate, Soyamidopropyl Betaine, and combinations thereof; and (iii) a non-ionic surfactant selected from the group consisting of Coco Glucoside, Lauryl Glucoside, Caprylyl/Capryl Glucoside, Decyl Glucoside, and combinations thereof, wherein the anionic surfactant is present in an amount of from about 0.5% to about 25% (e.g. about 5% to about 25%, about 10% to about 22%, about 0.5% to about 22% or about 5% to about 22%) by weight of the surfactant system, wherein the amphoteric surfactant is present in an amount of from about 0.5% to about 50% (e.g. about 5% to about 50%, about 35% to about 50%, about 0.5% to about 43% or about 5% to about 43%) by weight of the surfactant system, wherein the non-ionic surfactant is present in an amount of from about 0.5% to about 45% (e.g. about 5% to about 45%, about 25% to about 35%) by weight of the surfactant system, and wherein the total amount of the surfactant system present in the cosmetic composition is from about 1.5% to about 25% (e.g. about 5% to about 25%, about 10% to about 15%) by weight of the composition.

In one embodiment, the cosmetic composition of the invention comprises a cosmetically acceptable carrier and a surfactant system consisting of:

(i) an anionic surfactant selected from the group consisting of Disodium Laureth Sulfosuccinate, Disodium Lauryl Sulfosuccinate, Laureth-7 Citrate, Sodium Cocoyl Glutamate, Sodium Lauroyl Sarcosinate, Sodium Lauryl Glucose Carboxylate, and combinations thereof;

(ii) an amphoteric surfactant selected from the group consisting of Capryl/Capramidopropyl Betaine, Cocamidopropyl Betaine, Sodium Cocoamphoacetate, and combinations thereof; and (iii) a non-ionic surfactant selected from the group consisting of Coco Glucoside, Lauryl Glucoside, and combinations thereof, wherein the anionic surfactant is present in an amount of from about 0.5% to about 25% (e.g. about 5% to about 25%, about 10% to about 22%, about 0.5% to about 22% or about 5% to about 22%) by weight of the surfactant system, wherein the amphoteric surfactant is present in an amount of from about 0.5% to about 50% (e.g. about 5% to about 50%, about 35% to about 50%) by weight of the surfactant system, wherein the non-ionic surfactant is present in an amount of from about 0.5% to about 45% (e.g. about 5% to about 45%, about 25% to about 35%, about 0.5% to about 43% or about 5% to about 43%) by weight of the surfactant system, and wherein the total amount of the surfactant system present in the cosmetic composition is from about 1.5% to about 25% (e.g. about 5% to about 25%, about 10% to about 15%) by weight of the composition.

The cosmetic composition of the invention may comprise the surfactant system in an amount effective to produce an $\Delta L^*$ value of more than about 5, for example about 5.5, about 6, or about 6.5, and also in an amount effective to produce an L/D value of more than about 10. In the context of the invention, the $\Delta L^*$ value is indicative of the cleansing efficacy of the composition in which the higher the $\Delta L^*$ value, the higher the cleansing efficacy of the composition. It is generally perceived that an acceptable cleanser has an $\Delta L^*$ value of about 4 to 5, a good cleanser has an $\Delta L^*$ value of about 5 to 8 and a very good cleanser has an $\Delta L^*$ value of 8 or above. As a point of reference, a very good cleanser with an $\Delta L^*$ value of 8 or above is very effective at cleaning but the downside is that it is harsh on the skin. The L/D value is indicative of the harshness/irritant effect of the composition in which an L/D value greater than 10 means that the composition is considered to be non-irritating/mild. A suitable technique for measuring $\Delta L^*$ and L/D values is described in detail in the Examples section of the specification.

The invention makes use of a cosmetically acceptable carrier. The carrier may be water-based, oil-based, or emulsion-based.

In embodiments where the carrier is emulsion-based, the composition may be in the form of a water-in-oil, an oil-in-water, a water-in-oil-in-water or a oil-in-water-in-oil emulsion.

In embodiments where the carrier is water-based, water may be present at a level of about 40% or more, about 45% or more, about 50% or more, about 55% or more, or about 60% or more by weight of the composition.

The cosmetic composition of the invention may be provided in any form suitable for topical application to the skin and/or hair. The cosmetic composition of the invention may be delivered and/or applied to the skin and/or hair via any of the conventional formulations known to those skilled in the art. Typical formulation types of the present invention are liquids, creams, lotions, milks, mousses, gels, sprays, serum, foams, aerosols, and ointments.

In embodiments where the cosmetic composition is in the form of a water-in-oil emulsion, water may be present at a level of about 20% to about 60% by weight of the composition, about 20% to about 50% by weight of the composition, or about 35% to about 45% by weight of the composition. In one embodiment where the cosmetic composition is in the form of a water-in-oil emulsion, water is present at a level of about 35% to about 45% by weight of the composition.

In embodiments where the cosmetic composition is in the form of an oil-in-water emulsion, water may be present in an amount of about 40% to about 90% by weight of the composition or about 60% to about 95% by weight of the composition. In one embodiment where the cosmetic composition is in the form of an oil-in-water emulsion, water is present at a level of about 60% to about 95% by weight of the composition.

In addition to the carrier and the surfactant system, the cosmetic composition of the invention will generally further comprise other ingredients or excipients which will be well known to those skilled in the art.

The cosmetic composition of the invention may further comprise one or more humectants, including but not limited to glycerin, propylene glycol, propanediol, butylene glycol, pentylene glycol, hexylene glycol, hexanediol, dipropylene glycol, polyethylene glycol, sorbitol, sodium hyaluronate, urea, xylitol, lactate, fructose, glucose, mannose, xylose, honey, pyrrolidone, and carboxylic acid and salts thereof. When present, the one or more humectants may be present in the cosmetic composition in an amount of about 0.01% to about 20% by weight of the composition, about 0.1% to about 10%, or about 0.5% to about 7% by weight of the composition.

The cosmetic composition of the invention may further comprise one or more emollients, including but not limited to PPG-15 stearyl ether, ethylhexyl stearate, cetyl dimethicone, octyldodecanol, PPG-20 methyl glucose ether, isopropyl myristate, isopropyl paltimate, isopropyl laurate, isodecyl laurate, isodecyl neopentanoate, isohexadecane, pentaerythrityl tetraisostearate, caprylic/capric triglyceride, canola oil, sunflower oil (*Helianthus annus*), olive oil (*Olea europea*), cottonseed oil (*Gossypium herbaceum*), jojoba oil (*Simmondsia chinensis*), shea butter (*Butyrospermum parkii*), cocoa butter (*Theobroma cacao*), cupuacu butter (*Theobroma grandiflorum*), avocado oil (*Persea gratissima*), liquid paraffin, dimethicone, phenyl trimethicone, cyclopentasiloxane, dimethiconol and petrolatum. When present, the one or more emollients may be present in the cosmetic composition in an amount of about 0.01% to about 20% by weight of the composition, about 0.1% to about 10%, or about 0.5% to about 7% by weight of the composition.

The cosmetic composition may further comprise one or more emulsifiers, including but not limited to steareth-2, steareth-21, steareth-10, ceteareth-5, ceteareth-20, cetearyl glucoside, oleth-10, glyceryl stearate, polyglycerol-3 oleate, polyglyceryl-3 methylglucose distearate, sodium stearate, PEG-12 oleate, PEG-2 stearate, PEG-12 stearate, PEG-100 stearate, cetyl alcohol, cetearyl alcohol, potassium cetyl phosphate, cetearyl olivate, sorbitan olivate, PEG-80 sorbitan, sorbitan oleate, and/or sorbitan palmitate. In one embodiment, the cosmetic composition of the invention does not comprise sulphates as emulsifiers. In embodiments where one or more emulsifiers are present in the cosmetic composition, the one or more emulsifiers may be present in an amount of about 0.01% to about 5% or about 0.01% to about 2% by weight of the composition. In one embodiment, the cosmetic composition of the invention does not contain emulsifiers.

The cosmetic composition of the invention may further comprise one or more preservatives, including but not limited to, 2-bromo-2nitropropane-1,3-diol (bronopol, commercially available under the trade name Myacide®), benzyl alcohol, benzoic acid, sodium benzoate, diazolidinyl urea, imidazolidinyl urea, methyl paraben, phenoxyethanol, ethyl paraben, propyl paraben, sodium methyl paraben, sodium dehydroacetate, dehydroacetic acid, citric acid, polyhexamethylenebiguanide hydrochloride, isothiazolone, chlorhexidine digluconate, chlorphensin and/or sodium propyl paraben. In one embodiment, the cosmetic composition of the invention does not comprise parabens. In embodiments where one or more preservatives are present in the cosmetic composition, the one or more preservatives may be present in an amount of about 0.001% to about 10% by weight of the composition, about 0.01% to about 8% by weight of the composition, or about 0.1% to about 5% by weight of the composition. In one embodiment where one or more preservatives are present in the cosmetic composition, the one or more preservatives are present in an amount of about 0.05% to about 8% by weight of the composition.

The cosmetic composition of the invention may further comprise one or more chelating agents or sequestering agents, including but not limited to, ethylenediamine tetraacetic acid (EDTA) and salts thereof (e.g. dipotassium EDTA, disodium EDTA or tetrasodium EDTA), sodium phytate, trisodium ethylene diamine disuccinate, and/or tetrasodium glutamate diacetate. In embodiments where one or more chelating agents are present in the cosmetic composition, the one or more chelating agents may be present in an amount of about 0.001% to about 10% by weight of the composition, about 0.01% to about 8% by weight of the composition, or about 0.1% to about 5% by weight of the composition. In one embodiment where one or more chelating agents are present in the cosmetic composition, the one or more chelating agents are present in an amount of about 0.05% to about 8% by weight of the composition.

The cosmetic composition of the invention may further comprise one or more antioxidant agents, for example a polyphenolic antioxidant agent selected from the group consisting of extracts of mulberry (e.g. *Morus alba*), ginseng (e.g. *Panax ginseng*), raspberry, oregano (e.g. *Origanum vulgare*), green tea (e.g. green leaves of *Camellia sinensis*), white tea (e.g. *Camellia sinensis*), blueberry (e.g. *Vaccinium cyanococcus*), French maritime pine bark (e.g. *Pinus pinaster*, sold under the tradename of Pycnogenol), rosemary (e.g.

Rosmarinus officialis), grape, including grape seed (e.g. *Vitis vinifera*), fennel (e.g. *Foeniculi fructus*), *Caragana sinica*, majaoram (e.g. *Origanum majorana*), crocus (e.g. *Crocus sativus*), apple (e.g. *Malus domestica*), coffee, green coffee, cherry (e.g. *Prunus avium*), snow algae (e.g. *Chlamydomonas nivalis*), *Emblica* (e.g. *Pyllanthus emblica*), ginkgo (e.g. *Ginkgo biloba*), moringa (e.g. *Moringa oleilera*), ginger, magnolia (e.g. *Magnolioideae virginiana*), French saffron, edelweiss (e.g. *Leontopodium alpinium*), white lotus (e.g. *nymphaea alba*), turmeric root, marshmallow (e.g. *Althaea officianlis*), burdock (e.g. *Arctium lappa*), bilberry (e.g. *Vaccinium myrtillus*), cranberry (e.g. *Vaccinium oxycoccus*), pomegranate (e.g. *Punica granatum*), sage (e.g. *Salvia officianlis*), thyme (e.g. *Thymus vulgaris*), sunflower (e.g. *Helianthus annus*), wild carrot (e.g. *Daucus carota*), hop (e.g. *Humulus lupulus*), witch hazel (e.g. *Hamamelis*), oak (e.g. *Quercus*), *Camellia* (e.g. *Theacea*), red clover (e.g. *Tritolium pratense*), flax (e.g. *Linium usitatissiumum*), lemon (e.g. *Citrus limon*), birch (e.g. *Betula*), cornflower (e.g. *Centaurea cyanus*), geranium, *polygonum*, soy (e.g. *Glycine max*), *Sophora* and combinations thereof.

The cosmetic composition of the invention may further comprise one or more vitamins. For example, the cosmetic composition may further comprise vitamin B, vitamin B1 to vitamin B12, vitamin C, vitamin D, vitamin E, vitamin K, vitamin H, derivatives thereof, provitamins thereof (e.g. provitamin B5 (panthenol)), or combinations thereof. In embodiments where one or more vitamins are present in the cosmetic composition, the one or more vitamins may be present in an amount of about 0.0001% to about 50% by weight of the composition, about 0.001% to about 10% by weight of the composition, about 0.01% to about 8% by weight of the composition, or about 0.1% to about 5% by weight of the composition. In one embodiment where one or more vitamins are present in the cosmetic composition, the one or more vitamins are present in an amount of about 0.1% to about 5% by weight of the composition. In one embodiment where one or more vitamins are present, the vitamin is vitamin C or a derivative thereof.

The cosmetic composition of the invention may further comprise one or more antioxidants. These may be different to the polyphenolic antioxidant agents already present in the composition. In one embodiment where one or more such additional antioxidants are present in the cosmetic composition, the one or more additional antioxidants are present in an amount of from about 0.1% to about 5% by weight of the composition.

The cosmetic composition of the invention may further comprise one or more sunscreen agents, including but not limited to inorganic sunscreen agents (e.g. microfine titanium dioxide, microfine zinc oxide, iron oxides, talcs and/or boron nitride) and organic sunscreen agents (e.g. p-aminobenzoic acids, esters and derivatives thereof (e.g. 2-ethylhexyl p-dimethyl-aminobenzoate), methoxycinnamate esters (e.g., 2-ethylhexyl p-methoxycinnamate, 2-ethoxyethyl p-methoxycinnamate or α,β-di-(p-methoxycinnamoyl)-α'-(2ethylhexanoyl)-glycerin), benzophenones (e.g. oxybenzone), dibenzoylmethanes (e.g. 4-(tert-butyl)-4'-methoxydibenzoylmethane), 2-phenylbenzimidazole-5 sulfonic acid and salts thereof, alkyl-β,β-diphenylacrylates (e.g. alkyl α-cyano-β,β-diphenylacrylates such as octocrylene) triazines (such as 2,4,6-trianilino-(p-carbo-2-ethylhexyl-1-oxy)-1,3,5 triazine), and/or camphor derivatives (such as methylbenzylidene camphor). In embodiments where one or more sunscreen agents are present in the cosmetic composition, the one or more sunscreen agents may be present in an amount of about 0.01 to about 10% by weight of the composition.

The cosmetic composition of the invention may further comprise one or more pH adjusting agents, including but not limited to potassium hydroxide, sodium hydroxide, aminomethyl propanol, sodium citrate, and/or triethanolamine. The cosmetic composition of the invention may have a pH from about 3 to about 10, e.g. from about 4 to about 8, or from about 5 to about 7. Preferably, the pH of the composition is about 5 to about 5.5. In embodiments where one or more pH adjusting agents are present in the cosmetic composition, the one or more pH adjusting agents may be present in an amount of from about 0.01 to about 10% by weight of the composition.

The cosmetic composition of the invention may further comprise one or more thickeners or gelling agents. In one embodiment, the thickener is selected from the group consisting of Cocamide MEA, Glyceryl Laurate, Glyceryl Oleate, Laureth-3, Laureth-4, PEG-7 Glyceryl Cocoate, PEG-18 Glyceryl Oleate, PEG-18 Glyceryl Cocoate, PEG-120 Methyl Glucose Dioleate, PEG-120 Methyl Glucose Trioleate, PEG-150 Distearate, PEG-200 Hydrogenated Glyceryl Palmate, Acrylates Copolymer, Acrylates/C10-30 Alkyl Acrylate Crosspolymer, Acrylates Crosspolymer-4, Carbomer, Hydroxyethyl Cellulose, Magnesium Aluminium Silicate, Xanthan Gum, or combinations thereof. In one embodiment, the thickener is selected from the group consisting of Cocamide MEA, Glyceryl Laurate, Glyceryl Oleate, Laureth-3, Laureth-4, PEG-7 Glyceryl Cocoate, PEG-18 Glyceryl Oleate, PEG-18 Glyceryl Cocoate, PEG-120 Methyl Glucose Dioleate, PEG-120 Methyl Glucose Trioleate, PEG-150 Distearate, PEG-200 Hydrogenated Glyceryl Palmate, or combinations thereof. In embodiments where one or more thickeners/gelling agents are present in the cosmetic composition, the one or more thickeners/gelling agents may be present in an amount of about 0.01 to about 10% by weight of the composition.

The cosmetic compositions of the invention may further comprise one or more perfumes and/or colourings.

The cosmetic compositions of the invention may further comprise bisabolol and/or panthenol.

In the present application, the term "about" may encompass ±10%, such as ±5%, e.g. ±2% or ±1%.

The skilled person will understand that optional features of one embodiment or aspect of the invention may be applicable, where appropriate, to other embodiments or aspects of the invention.

There now follows by way of example only a description of the present invention with reference to the accompanying drawings, in which:

FIG. 1 shows a list of example cosmetic compositions according to the invention (all amounts are expressed as weight % based on the total weight of the composition (% w/w)); and FIG. 2 is a graph showing cleansing efficacy and mildness of various cleansers, including Example formulations 1 and 2.

EXAMPLES

Embodiments of the invention will now be described in more detail, by way of example only.
Cleansing Efficacy Testing
For each cleanser tested:
An even layer of foundation was applied to an acetate plastic sheet backed with white paper using a draw down machine fitted with a 12 μm bar and operating at speed setting 4. The sheet was allowed to dry at room temperature for 16 hours, before the colour of the foundation layer was measured at a marked position using an X-Rite Color i7 Spectrophotometer in reflectance mode. The acetate sheet was then placed again on the draw down apparatus and the draw down bar lifted so that it travelled without touching the surface of the sheet.

The surfactant product sample to be tested was dissolved in purified water in a concentration of 5.0% w/w. 2 ml of this solution was then applied to a cotton wool pad secured to the long side of a metal weight of 141 g and with dimensions of 130×23×23 mm. The metal weight was then immediately placed onto the acetate sheet with the cotton wool pad on the underside, in contact with the sheet.

The draw down machine was then immediately engaged at speed setting 4, pushing the weight down the sheet from top to bottom; this allowed the solution soaked cotton wool pad to remove foundation from the sheet.

The sheet was then analysed spectrophotometrically a second time, using an X-Rite Color i7 Spectrophotometer in reflectance mode at the same position on the acetate sheet as prior to the mechanical cleansing.

The spectrophotometer measures three parameters L*, a*, and b* of each sheet which describe the colour in terms of the CIELAB colour space. The difference between these values before and after cleansing (ΔL*, Δa*, Δb*) was recorded and used to assess the cleansing performance. The larger ΔL* is, the more negative Δa* and Δb* are. This would be expected as ΔL* is a measure of the change in lightness; a positive ΔL* represents a lightening caused by the foundation being removed from the sheet (as the sheet has a white backing). Δa* and Δb* measure changes in shade, so negative values represent a shift towards pure white due to a reduction in the pigment quantity present on the sheet after cleansing.

The difference between the L* (lightness) values before and after the cleansing process gives a ΔL* value for the sample. The higher the ΔL* value, the more foundation has been removed from the acetate sheet, and the more effective the sample can be said to be at cleansing.

The procedure was repeated three times for each sample, and the mean value of the three ΔL* values calculated to give an overall ΔL* value for the sample.

Harshness Testing

Harshness testing was carried out using an in-vitro method using red blood cells as an analogue for skin cells, as similar lipids and proteins are found in membranes of both cells.

For each cleanser tested:
A buffered sample of blood cells was incubated for 10 minutes with a cleanser solution.
The mixture was centrifuged and the level of haemoglobin present in the supernatant was determined by UV/Visible Spectroscopy.
The quantity of haemoglobin present is proportional to the number of cells which have been destroyed by the cleanser.
Two values result from this method: the H 50 is the concentration of cleanser at which 50% of the cells in the sample are destroyed (ppm). The DI value is a measure of how much the haemoglobin released is attacked by the cleanser in relation to a Sodium Dodecyl Sulfate (very harsh surfactant) standard (%).

In order to rank the products according to harshness, the H 50 and DI results were combined by dividing the H 50 by the DI to give an L/D value. The lower this value, the harsher the cleanser (i.e. low H 50 with high DI). The higher this value, the milder the cleanser. A value above 10 was indicative of a non-irritating/mild product. The results were displayed on a log scale.

Results

FIG. 2 shows that Example formulations 1 and 2 according to the invention achieve an optimal balance between cleansing efficacy and mildness, possessing good cleansing abilities (ΔL* value of 5.99) as well as being mild (L/D value of 63). This is in contrast to competitor products A and B which are effective cleansers (ΔL* values of 9.09 and 6.36, respectively) but are harsh and not mild (L/D values of 0.21 and 1.1, respectively), and competitor products C and D which are mild (L/D values of 41 and 281, respectively) but not effective at cleansing (ΔL* values of 2.93 and 4.05, respectively).

The surfactant composition of Example formulations 1 and 2 is presented in the Table below:

| Type of Surfactant | Surfactant Name | Concentration within Surfactant System (w/w) | |
|---|---|---|---|
| | | Formulation 1 | Formulation 2 |
| Anionic | Disodium laureth sulfosuccinate | 20.2% | 21.0% |
| Amphoteric | Cocamidopropyl betaine | 28.9% | 24.9% |
| | Sodium cocoamphoacetate | 16.9% | 13.9% |
| Non-ionic | Lauryl glucoside | 26.9% | 34.5% |
| | Coco glucoside | 7.1% | 5.5% |

The surfactant systems described above made up 14.868% by weight of Formulation 1 and 19.195% by weight of Formulation 2.

The invention claimed is:
1. A cosmetic composition comprising a cosmetically acceptable carrier and a surfactant system consisting of:
   (i) one or more anionic surfactant(s), wherein the anionic surfactant is selected from the group consisting of Disodium Laureth Sulfosuccinate, Disodium Lauryl Sulfosuccinate, Laureth-7 Citrate, Sodium Cocoyl Glutamate, Sodium Lauroyl Sarcosinate, Sodium Lauryl Glucose Carboxylate, and combinations thereof;
   (ii) one or more amphoteric surfactant(s), wherein the amphoteric surfactant is selected from the group consisting of Capryl/Capramidopropyl Betaine, Cocoamidopropyl Betaine, Sodium Cocoamphoacetate, and combinations thereof; and
   (iii) one or more non-ionic surfactant(s), wherein the non-ionic surfactant is selected from the group consisting of Coco Glucoside, Lauryl Glucoside, Caprylyl/Capryl Glucoside, Decyl Glucoside, and combinations thereof,
   wherein the one or more anionic surfactant(s) are present in an amount of from about 15% to about 25% by weight of the surfactant system,
   wherein the one or more amphoteric surfactant(s) are present in an amount of from about 35% to about 50% by weight of the surfactant system,
   wherein the one or more non-ionic surfactant(s) are present in an amount of from about 20% to about 45% by weight of the surfactant system,
   wherein the total amount of the surfactant system present in the cosmetic composition is from about 1.5% to about 25% by weight of the composition, wherein the cosmetic composition does not comprise a cationic surfactant, wherein the composition comprises only those surfactants present in the surfactant system, and wherein the surfactant(s) are defined as molecules having both hydrophilic groups and hydrophobic groups.

2. The cosmetic composition of claim 1, wherein the non-ionic surfactant is present in an amount of:

from about 25% to about 40% by weight of the surfactant system.

3. The cosmetic composition of claim 1, wherein the surfactant system is present in an amount of:
   (a) from about 5% to about 25% by weight of the composition;
   (b) from about 5% to about 20% by weight of the composition;
   (c) from about 10% to about 20% by weight of the composition; or
   (d) from about 10% to about 18% by weight of the composition.

4. A method of cosmetic cleansing treatment of the skin and/or hair comprising the step of applying the cosmetic composition as defined in claim 1 to the skin and/or hair.

5. A method of using the cosmetic composition as defined in claim 1 by applying the cosmetic composition as a topical application for cleansing the skin and/or hair, and/or for removing makeup.

6. A method of cosmetically treating skin damage as a result of pollution insult or of cosmetically preventing the detrimental effects of pollution to the skin, said method comprising cleansing the skin with an effective amount of the cosmetic composition as defined in claim 1.

* * * * *